United States Patent [19]

Girard et al.

[11] Patent Number: 4,663,307

[45] Date of Patent: May 5, 1987

[54] ANTI-ALLERGIC AND ANTI-THROMBOEMBOLIC 6H-DIBENZ-[B,E][1,4]-OXATHIEPIN DERIVATIVES, COMPOSITIONS, AND METHOD OF USE THEREFOR

[75] Inventors: Yves Girard, Pierrefonds; Joshua Rokach, Laval; Pierre Hamel, Vimont, all of Canada

[73] Assignee: Merck Frosst Canada, Inc., Quebec, Canada

[21] Appl. No.: 655,783

[22] Filed: Oct. 1, 1984

Related U.S. Application Data

[63] Continuation-in-part of Ser. No. 545,564, Oct. 26, 1983, abandoned.

[51] Int. Cl.[4] .................... A61K 31/39; C07D 327/02
[52] U.S. Cl. ........................................ 514/2; 514/223; 514/248; 514/336; 514/420; 514/423; 549/10
[58] Field of Search ...................... 549/10; 514/431, 2, 514/223, 248, 336, 420, 423

[56] References Cited

U.S. PATENT DOCUMENTS 3,978,052 8/1976 Stoss et al. ........................... 549/10

FOREIGN PATENT DOCUMENTS 0029587 6/1981 European Pat. Off .............. 549/12

OTHER PUBLICATIONS

Hafliger et al., *Iminodibenzyl and Related Compounds*, Ciba Geigy, 1985, pp. 35-43.
Gordon, Textbook "*Psychopharmacological Agents*, 1964, Academic Press, New York, N.Y. pp. 5-8.
March, "Advanced Organic Chemistry", pp. 796-797, John Wiley and Sons, (1985).

*Primary Examiner*—John M. Ford
*Assistant Examiner*—J. G. Mullins
*Attorney, Agent, or Firm*—C. M. Caruso; H. J. Pfeiffer

[57] ABSTRACT

Novel 6H-dibenz[b,e][1,4]oxathiepin derivatives of the Formulae I and IA are employed in the treatment and control of allergic conditions such as allergic asthma.

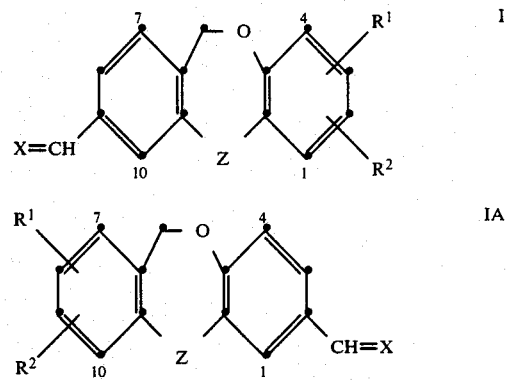

23 Claims, No Drawings

ANTI-ALLERGIC AND ANTI-THROMBOEMBOLIC 6H-DIBENZ-[B,E][1,4]-OXATHIEPIN DERIVATIVES, COMPOSITIONS, AND METHOD OF USE THEREFOR

This application is a continuation-in-part of U.S. Ser. No. 545,564, filed Oct. 26, 1983, now abandoned.

This invention relates to prostaglandin antagonists useful in treating a variety of conditions in mammals (especially humans), such as allergic asthma where excessive contractile activity of prostaglandins and prostaglandin biosynthetic intermediates occur. These prostaglandin antagonists are also useful in reducing the formation of thrombi. Thus, the compounds of this invention are useful in the treatment and/or prevention of thromboembolic diseases, particularly arterial thrombosis which has been reported to be initiated by injury of the blood vessel wall [J. F. Mustard, et al., *Drugs*, 9, 19-76 (1975); J. C. McGiff, *Adv. Intern. Med.*, 25, 199-216 (1980)]. These prostaglandin antagonists are a novel group of 6 H-dibenz[b,e][1,4]oxathiepins having the following structural formulae:

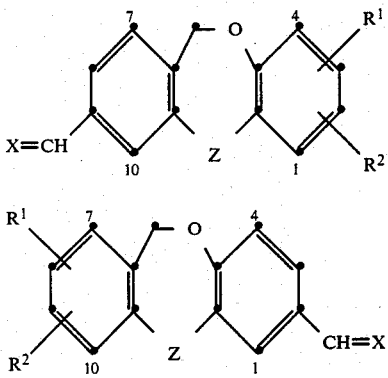

wherein:

Z is thio, sulfinyl, or sulfonyl;

$R^1$ and $R^2$ are each independently hydrogen, halogen, amino, $C_1$ to $C_4$ alkyl, $C_1$ to $C_4$ alkylthio, $C_1$ to $C_4$ alkoxy, thiol, $C_1$ to $C_4$ alkylsulfinyl, $C_1$ to $C_4$ alkylsulfonyl, trifluoromethyl, trifluoromethylthio, cyano, nitro, $C_1$ to $C_4$ alkyl or dialkylamino, aralkyl (for example, benzyl or phenethyl), or hydroxyalkyl (for example, $CH_3CHOH$), or $R^1$ and $R^2$ are joined together to form a polymethylene chain of 3 or 4 carbon atoms with or without a hydroxy or keto functionality;

X is oxo, N—$R^3$, wherein $R^3$ is hydrogen, $C_1$ to $C_4$ alkyl, aryl, hydroxy, $C_1$ to $C_4$ alkoxy, $C_1$ to $C_5$ alkanoyloxy, amino, $C_1$ to $C_4$ alkylamino or dialkylamino wherein each alkyl group has 1 to 4 carbons; or a group of the formula:

wherein each Y is independently O or S or $NR^6$ wherein $R^6$ is H, $C_1$ to $C_4$ alkyl, lower alkanoyl, benzoyl, trifluoroacetyl or CN; and $R^4$ and $R^5$ are each independently hydrogen or $C_1$ to $C_4$ alkyl and the broken line between $R^4$ and $R^5$ represents an optional bond when $R^4$ and $R^5$ are not hydrogen; and the pharmaceutically acceptable salts thereof.

As used herein, the term halogen (or halo) includes chlorine, bromine, iodine, and fluorine. Unless otherwise specifically stated, the terms loweralkyl and loweralkoxy include straight and branched chain alkyl and alkoxy groups having 1 to 5 carbon atoms in the alkyl or alkoxy moiety such as, for example, methyl, ethyl, n-propyl, isopropyl, n-butyl, methoxy, ethoxy, n-propoxy, and isobutoxy. The term loweralkanoyl includes straight or branched chain alkanoyl groups having 1 to 5 carbon atoms in the alkanoyl moiety such as, for example, formyl, acetyl, propanoyl, isobutyryl and pivaloyl. The term aralkyl includes straight or branched chain alkyl radicals of 1 to 4 carbon atoms having one of the hydrogens replaced by an aryl group. The term aryl includes phenyl and substituted phenyl groups, including halophenyl such as chloro, bromo, iodo, and fluorophenyl, nitrophenyl, aminophenyl, hydroxyphenyl, loweralkylphenyl, and the like.

These dibenzoxathiepin derivatives antagonize the actions of contractile prostaglandins, such as $PGF_{2\alpha}$, $PGH_2$, and $TXA_2$. The use of agents which act as prostaglandin antagonists offers new approaches to therapy in a number of disease states. For example, certain prostaglandins, such as $PGF_{2\alpha}$, PGG, and $PGH_2$, are potent contractants of bronchial muscle. Indeed human asthmatics have been shown to be especially sensitive to the bronchial constricting action of $PGF_{2\alpha}$.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, premature abortion, and dysmenorrhea.

In addition to the prostaglandin antagonist actions, the dibenzoxathiepins of this invention are antagonists of slow reacting substance of anaphylaxis (SRS-A). This contractile substance is released in the lung tissue in allergic asthma, and antagonism of its actions contributes to alleviation of this disease.

The dibenzoxathiepins of Formula I of this invention are prepared according to the following general reaction scheme:

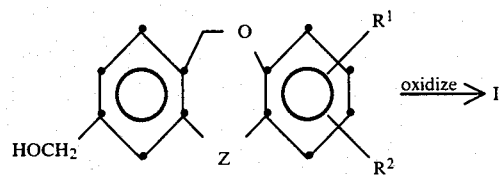

where $R^1$, $R^2$ and Z are as defined above. Formula IA is prepared similarly using the appropriate starting material.

As shown in the above reaction scheme, an appropriately substituted 2-hydroxymethyl dibenzoxathiepin is oxidized to the correspondingly substituted dibenzoxathiepin-2-carboxaldehyde by treatment with an oxidizing agent, such as pyridinium chlorochromate, tert-butyl chromate, potassium dichromate, lead tetracetate or 2,3-dichloro-5,6-dicyanoquinone (DDQ). Each reagent is effective for bringing about the desired oxidation to a carboxaldehyde substituent but pyridinium chlorochromate is preferred for the oxidation of the hydroxymethyl group to a carboxaldehyde group. The oxidation is conducted in a solvent which is inert under the reaction conditions and may be either volatile or nonvolatile. Ethyl ether or other loweralkyl ethers are satisfactory and tetrahydrofuran is a commonly preferred solvent. A more preferred type of solvent is a halogenated hydrocarbon such as dichloromethane, 1,2-dichloroethane, chloroform, etc.

The chosen oxidation reagent is employed in a slight excess over the stoichiometric amount needed in order to insure completeness of reaction. The reaction is maintained at a temperature between 0° and 100° C. or the reflux temperature of the solvent. Most alcohols are oxidized relatively completely at room temperature (25° C.) and in a relatively short time (approximately 1 hour), and therefore the oxidation is usually conducted by stirring the alcohol for a period of from 30 minutes to 12 hours at a temperature of from 10° to 40° C. Following the completion of the reaction, the product is isolated by the addition of water and extraction into ether. The ether extract is evaporated to obtain the residual product which is purified by chromatography or recrystallized from an appropriate solvent.

Alternatively, an aldehyde derivative can be obtained by treatment of an appropriate nitrile with a nickel catalyst such as a 1:1 alloy of nickel and aluminium, in an acidic medium such as formic acid. It is also possible to transform an alkanoyl ester; for example a methyl or ethyl ester, into the corresponding aldehyde through the action of a dialkyl aluminium hydride reagent such as di-isobutyl aluminium hydride, using as solvent a dialkyl or cyclic ether, such as diethyl ether or tetrahydrofuran.

The dibenzoxathiepin-2-carboxaldehyde-11-oxide or derivatives thereof are alternatively prepared by oxidation of the corresponding dibenzoxathiepin-2-carboxaldehyde with organic peroxides such as peroxy acids like m-chloroperbenzoic acid or hydrogen peroxide in acetic acid. The oxidation can be carried further, if an additional equivalent of oxidizing agent is employed, to produce the corresponding dibenzoxathiepin-11,11-dioxides. It will be apparent to one skilled in the art that variations in these preparative schemes will allow one to prepare a variety of substituted dibenzoxathiepin-2-carboxaldehydes.

The compounds of Formulae I and Ia wherein X is other than oxygen may be prepared by methods well known to one skilled in the art. Thus, oximes or Schiff bases are prepared by treating I or Ia (X=oxo) with hydroxylamine or a primary amine, respectively; acetals are prepared by treating the aldehydes with a lower alkanol in the presence of a mineral acid or with a reagent such as 2-methoxy-1,3-dioxolane in the presence of a mineral acid.

Some of the compounds of Formulae I and IA are capable of existing as optical isomers which may be resolved by known procedures into their enantiomers. Each of the enantiomorphic isomers may exhibit variation in biological potency and it is understood that the present invention includes the racemic mixture as well as the individual resolved optical isomers.

Preferred embodiments of this invention are the compounds of Formula IA wherein Z is sulfinyl or sulfonyl, $R^2$ is hydrogen and $R^1$ is at position 8 or 9 and is fluoro, chloro, bromo, amino or hydrogen, and the compounds of Formula I wherein Z is sulfinyl or sulfonyl, $R^2$ is hydrogen and $R^1$ is at position 2 or 3 and is fluoro, chloro, bromo, amino or hydrogen.

More preferred embodiments of this invention are the compounds of Formula IA wherein Z is sulfinyl or sulfonyl, $R^2$ is hydrogen, $R^1$ is at position 8 or 9 and is fluoro, chloro, bromo, amino, or hydrogen and X is oxo, and the compounds of Formula I wherein Z is sulfinyl or sulfonyl, $R^2$ is hydrogen, $R^1$ is at position 2 or 3 and is fluoro, chloro, bromo, amino or hydrogen, and X is oxo.

Particularly preferred embodiments of this invention are the compounds of Formula IA wherein Z is sulfonyl, $R^2$ is hydrogen and $R^1$ is at position 8 or 9 and is fluoro, chloro, bromo, amino, or hydrogen, and X is oxo, and the compounds of Formula I wherein Z is sulfonyl, $R^2$ is hydrogen, $R^1$ is at position 2 or 3 and is fluoro, chloro, bromo, amino or hydrogen, and X is oxo.

The starting materials, the alcohols, are described in copending application Case 16789IA, U.S. Ser. No. 520,053, filed Aug. 5, 1983, and European Patent Application No. 83305753.2, Publication No. 0 105 692, which are hereby incorporated herein by reference. In addition, preparative examples of some representative starting materials are found herein.

Generally, to prepare the starting materials of Formula IA, an appropriately substituted o-iodobenzoic acid is reacted with o-methoxythiophenol in the presence of copper powder and aqueous potassium hydroxide in order to obtain the corresponding 2-(o-methoxyphenylthio)benzoic acid. The reaction is carried out at reflux and usually requires 2 to 5 hours for completion. Upon recovery, the acid product may be converted into the corresponding lower alkanol ester by refluxing with a lower alkanol in the presence of a strong acid such as sulfuric acid, hydrochloric acid, trifluoroacetic acid and the like. The ester product then is treated with dichloromethyl methylether in the presence of titanium tetrachloride to form the corresponding 3-(o-carboloweralkoxyphenylthio)-4-methoxybenzaldehyde which then is demethylated with hydrogen bromide in glacial acetic acid to form the corresponding 3-(o-carboxyphenylthio)-4-hydroxybenzaldehyde. The aldehyde so produced then is treated with hydroxylamine hydrochloride in the presence of sodium formate and formic acid to form the corresponding 3-(o-carboxyphenylthio)-4-hydroxybenzonitrile which is treated with dicyclohexylcarbodiimide (DCC) to form the corresponding 2-cyano-6H-6-oxo-dibenz[b,e][1,4]oxathiepin. The 2-cyano-oxathiepin product then is treated with an alkali metal borohydride to form the corresponding 3-(o-hydroxymethylphenylthio)-4-hydroxybenzonitrile which is reacted with dicyclohexylcarbodiimide to form the desired 2-cyano-6H-dibenz[b,e][1,4]oxathiepin, which is then processed, via a combination of oxidation and hydrolysis, to the carboxylic acid derivative having the desired oxidation state on the sulfur.

Alternatively, an appropriately substituted o-mercaptobenzyl alcohol is reacted with 3-iodo-4-hydroxybenzoic acid in the presence of copper powder and aqueous potassium hydroxide in order to obtain the corresponding 3-(o-hydroxymethyl phenylthio)-4-hydroxybenzoic acid. The reaction is carried out at reflux and generally requires 6 to 24 hours for completion. After isolation the acid product may be converted into the corresponding lower alkanol ester by refluxing with a lower alkanol in the presence of a strong acid such as sulfuric acid, hydrochloric acid, trifluoroacetic acid and the like. The ester product then is cyclized, for example through the use of diethyl azo dicarboxylate in the presence of triphenyl phosphine, in an inert solvent, preferably an ether such as tetrahydrofuran, or through the use of a dehydrating agent such as dicyclohexyl carbodiimide, to afford the corresponding appropriately substituted 6H-dibenz [b,e][1,4]oxathiepin-2-carboxylate, which is then hydrolyzed through the action of an aqueous solution of a strong alkali such as sodium or potassium hydroxide, followed by acidification to yield the corresponding carboxylic acid derivative.

To prepare Formula I derivatives, an appropriately substituted o-amino thiophenol is reacted with 2-chloro-4-nitrobenzoic acid in the presence of cuprous oxide in quinoline, to produce the corresponding 2-(o-aminophenylthio)-4-nitrobenzoic acid. The amine function is then diazotized through the action of sodium nitrite in dilute aqueous sulfuric acid, and the diazonium salt transformed into the corresponding phenol by heating in 50% aqueous sulfuric acid. The precipitated product is collected, and transformed, preferably by the action of borane in tetrahydrofuran, into the corresponding 2-(o-hydroxyphenylthio)-4-nitrobenzyl alcohol. Compounds of this type are cyclized through the use of an appropriate dehydrating agent, such as dicyclohexyl carbodiimide, to the corresponding 9-nitro-6H-dibenz[b,e][1,4]oxathiepin. The nitro function is transformed into an amine by one of several reducing agents, the reagent of choice being stannous chloride in a mixture of concentrated hydrochloric acid and tetrahydrofuran. The amino compound thus obtained is diazotized by treatment with sodium nitrite in aqueous hydrochloric acid, then transformed into the corresponding nitrile on addition of the diazonium salt to a mixture of cuprous cyanide and potassium cyanide in aqueous medium. The 9-cyano compounds thus obtained are then processed, via a combination of oxidation and hydrolysis, to the carboxylic acids having the desired oxidation state on the sulfur.

The carboxylic acid derivative is then reduced to the corresponding 2-hydroxymethyl (or 9-hydroxymethyl) derivative by treatment with an alkali metal aluminum hydride such as lithium aluminum hydride, diborane, alkali metal borohydride, or alkali metal deuteride.

The oxathiepins of Formulae I and IA are useful in the treatment and prophylaxis of human or warm-blooded animal disease conditions where excessive undesirable contractile activity of prostaglandins, such as $PGF_{2\alpha}$, or prostaglandin biosynthetic intermediates contribute. In particular, they are of value in the treatment and control of allergic conditions such as asthma. It will be understood that in this paragraph and in the discussion of methods of treatment which follows, references to the compounds of Formulae I and IA are also meant to include the corresponding pharmaceutically acceptable salts.

The magnitude of a prophylactic or therapeutic dose of compounds of Formulae I and IA will, of course, vary with the nature and the severity of the condition to be treated and with the particular compound of Formulae I and IA and its route of administration. In general, the dose range lies within the range of 0.2 mg to 100 mg per kg body weight per day.

The pharmaceutical compositions of the present invention comprise a compound of Formulae I and/or IA as an active ingredient, and may also contain pharmaceutically acceptable carrier and optionally other therapeutic ingredients. In addition to the compounds of Formulae I and IA, the pharmaceutical compositions can also contain other active ingredients, such as non-steroidal anti-inflammatory agents e.g. indomethacin, ibuprofen, sulindac, fenbufen, and the like, peripheral analgesic agents such as zomepirac, diflunisal and the like or cyclooxygenase inhibitors. They may also contain inhibitors of the biosynthesis of the leukotrienes. Compounds of this type are disclosed in copending Case 16876, U.S. Ser. No. 459,924, filed Jan. 21, 1983, the disclosure of which is hereby incorporated herein by reference, and others known in the art. These pharmaceutical compositions may also contain antihistaminic agents such as benadryl, dramamine, histadyl, phenergan and the like. Other active ingredients for combination with Formulae I or IA include leukotriene antagonists such as those described in U.K. Patent Application No. 2,058,785; and European Patent Application Nos. 56,172 and 61,800, the disclosure of these two applications being hereby incorporated herein by reference.

These pharmaceutical compositions containing Formulae I or IA compounds and a second active ingredient are another embodiment of the invention. The weight ratio of the Formulae I or IA compound to the second active ingredient may be varied and may range from 10:1 to about 1:10. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

An embodiment of the invention is a cardiovascular composition useful for treating arterial thrombosis which comprises an antithrombotic dibenzoxathiepin compound of the Formula I or IA.

A further embodiment of the invention is a cardiovascular composition useful for treating arterial thrombosis which comprises: (1) the antithrombotic Formula I or IA compound defined above; and, (ii) an angiotensin converting enzyme (ACE) inhibitor compound. Examples of such ACE inhibitors are: carboxyalkyl dipeptide derivatives; [1-(3-mercapto-2-methyl-1-oxopropyl)-L-proline], also known as captopril; 2-[N-(S)-1-ethoxycarbonyl-3-phenylpropyl)-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)-glycine; 1-(N-[(S)-1-ethoxycarbonyl-3-phenylpropyl]-L-alanyl)-cis,syn-octahydro-(H-indole-2-S)-carboxylic acid; 2-(N-[(S)-1-ethoxycarbonyl-3-phenylpropyl]-L-alanyl)-1,2,3,4-tetrahydroiso-isoquinoline-3(S)-carboxylic acid; and, 1-carboxymethyl-3(S)-(1(S)-ethoxycarbonyl-3-phenylpropylamino)-2,3,4,5-tetrahydro-1H[1]-benzazepine-2-one.

In particular, the class of ACE inhibitors which have been found to have a potentiating effect when used in combination with the Formula I or IA compounds are those disclosed in U.S. Pat. No. 4,374,829, which also discloses methods for their preparation and which patent is incorporated herein by reference and which compounds are generally represented by the Formula VI:

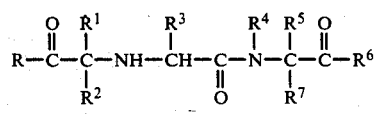

wherein
R and $R^6$ are the same or different and are hydroxy, lower $C_1$-$C_8$ alkoxy;
lower $C_1$-$C_8$ alkenoxy;
dilower $C_1$-$C_8$ alkylamino lower $C_1$-$C_8$ alkoxy (dimethylaminoethoxy):
acylamino lower $C_1$-$C_8$ alkoxy (acetylaminoethoxy);
acyloxy lower $C_1$-$C_8$ alkoxy (pivaloyloxymethoxy);
aryloxy, wherein the aryl is $C_6$ or $C_{10}$ such as phenoxy;
arlower $C_1$-$C_8$ alkoxy, such as benzyloxy; substituted aryloxy or substituted
arlower-$C_1$-$C_8$ alkoxy wherein the aryl is $C_6$ or $C_{10}$ and the substituent is methyl, halo or methoxy; amino;
lower $C_1$-$C_8$ alkylamino;
dilower $C_1$-$C_8$ alkylamino;
hydroxyamino;
arlower $C_1$-$C_8$ alkylamino wherein the aryl group is $C_6$-$C_{10}$ such as benzylamino;
$R^1$ is hydrogen;
hydrocarbon of from 1 to 20 carbon atoms which include branched and unsaturated (such as allyl) groups;
$C_3$-$C_{10}$ cycloalkyl;
substituted lower $C_1$-$C_8$ alkyl wherein the substituent can be halo, hydroxy, lower $C_1$-$C_8$ alkoxy, aryloxy wherein the aryl is $C_6$-$C_{10}$ such as phenoxy, amino, dilower $C_1$-$C_8$ alkylamino, acylamino such as acetamido and benzamido, arylamino wherein the aryl is $C_6$ or $C_{10}$, guanidino, imidazolyl, indolyl, mercapto, lower $C_1$-8 alkylthio, arylthio wherein the aryl is $C_6$ or $C_{10}$ such as phenylthio, carboxy or carboxamido, carbolower $C_1$-$C_8$ alkoxy;
aryl of $C_6$-$C_{10}$ such as phenyl or naphthyl;
substituted aryl of $C_6$-$C_{10}$ such as phenyl wherein the substituent is lower $C_1$-$C_8$ alkyl, lower $C_1$-$C_8$ alkoxy or halo,
unsubstituted or substituted arloweralkyl, arloweralkenyl, heteroarlower alkyl, or heteroarlower alkenyl, wherein aryl groups are $C_6$ or $C_{10}$, the alkyl groups are $C_2$-$C_8$, and the heteroatoms are one of O, N or S and the the substituent(s) is halo, dihalo, lower $C_1$-$C_8$ alkyl, hydroxy, lower $C_1$-$C_8$ alkoxy, amino, aminomethyl, acylamino (acetylamino or benzoylamino) dilower $C_1$-$C_8$ alkylamino, lower $C_1$-$C_8$ alkylamino, carboxyl, halolower $C_1$-$C_8$ alkyl, cyano or sulfonamido;
arlower $C_1$-$C_8$ alkyl or heteroarlower $C_1$-$C_8$ alkyl wherein the aryl group is $C_6$ or $C_{10}$ and the heteroatom is one of O, N or S, substituted on the alkyl portion by amino or acylamino (acetylamino or benzoylamino);
$R^2$ and $R^7$ are the same or different and are hydrogen or lower $C_1$-$C_8$ alkyl;
$R^3$ is hydrogen, lower $C_1$-$C_8$ alkyl, phenyl lower $C_1$-$C_8$ alkyl, aminomethyl phenyl lower $C_1$-$C_8$ alkyl, hydroxy phenyl lower $C_1$-$C_8$ alkyl, hydroxy lower $C_1$-$C_8$ alkyl, acylamino lower $C_1$-$C_8$ alkyl (such as benzoylamino lower $C_1$-$C_8$ alkyl, acetylamino lower $C_1$-$C_8$ alkyl), amino lower $C_1$-$C_8$ alkyl, dimethylamino lower $C_1$-$C_8$ alkyl, halo lower $C_1$-$C_8$ alkyl, guanidino lower $C_1$-$C_8$ alkyl, imidazolyl lower $C_1$-$C_8$ alkyl, indolyl lower $C_1$-$C_8$ alkyl, mercapto lower $C_1$-$C_8$ alkyl, lower $C_1$-$C_8$ alkyl thio lower $C_1$-$C_8$ alkyl;
$R^4$ is hydrogen or lower $C_1$-$C_8$ alkyl;
$R^5$ is hydrogen, lower $C_1$-$C_8$ alkyl, phenyl, phenyl lower $C_1$-$C_8$ alkyl, hydroxy phenyl lower $C_1$-$C_8$ alkyl, hydroxy lower $C_1$-$C_8$ alkyl, amino lower $C_1$-$C_8$ alkyl, guanidino lower $C_1$-$C_8$ alkyl, imidazolyl lower $C_1$-$C_8$ alkyl, indolyl lower $C_1$-$C_8$ alkyl, mercapto lower $C_1$-$C_8$ alkyl or lower $C_1$-$C_8$ alkyl thio lower $C_1$-$C_8$ alkyl; or, $R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, lower $C_{1-C_8}$ alkoxy, lower $C_1$-$C_8$ alkyl or dilower $C_1$-$C_8$ alkyl; and, the pharmaceutically acceptable salts thereof.

Preferred ACE inhibitor compounds of Formula VI are those wherein:
R and $R^6$ can each independently be hydroxy, lower alkoxy, lower alkenoxy, arloweralkyloxy, amino, diloweralkylamino lower alkoxy, acylamino lower alkoxy or acyloxy lower alkoxy;
$R^1$ is hydrogen,
alkyl of from 1 to 20 carbon atoms, including branched, cyclic and unsaturated alkyl groups;
substituted lower alkyl wherein the substituent is halo, hydroxy, lower alkoxy, aryloxy, amino, loweralkylamino, diloweralkylamino, acylamino, arylamino, guanidino, imidazolyl, indolyl, mercapto, loweralkylthio, arylthio, carboxy, carboxamido or carbolower alkoxy;
phenyl;
substituted phenyl wherein the substituent is lower alkyl, lower alkoxy or halo;
arloweralkyl or heteroaryloweralkyl arloweralkenyl or heteroarloweralkenyl, substituted arloweralkyl, substituted heteroarylloweralkyl, substituted arloweralkenyl or substituted heteroarloweralkenyl;
wherein the substituent is halo or dihalo lower alkyl, hydroxy, lower alkoxy, amino, aminomethyl, acylamino, diloweralkylamino, loweralkylamino, carboxyl, halo alkyl, cyano or sulfonamido;
arloweralkyl or heteroarloweralkyl substituted on the alkyl portion by amino or acylamino;
$R^2$ and $R^7$ are hydrogen;
$R^3$ is lower alkyl, amino lower alkyl, imidazolyl, lower alkyl, halo lower alkyl;
$R^4$ and $R^5$ are joined to form an alkylene bridge of from 2 to 4 carbon atoms or an alkylene bridge of from 2 or 3 carbon atoms and one sulfur atom or an alkylene bridge of from 2 to 3 carbon atoms and one sulfur atom or an alkylene bridge of from 3 to 4 carbon atoms containing a double bond or an alkylene bridge of from 3 to 4 carbon atoms containing a double bond or an alkylene bridge as above substituted with hydroxy, lower alkoxy or lower alkyl; or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl, or thiazolyl.

More preferred are those antihypertensive compounds of Formula VI wherein:
R and $R^6$ can each independently be hydroxy, lower alkoxy, lower alkenoxy, arloweralkyloxy, amino, diloweralkylamino lower alkoxy, acylamino lower alkoxy or acyloxy lower alkoxy;
$R^1$ is alkyl having from 1-8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1–3 carbon atoms, substituted aralkyl or heteroaralkyl wherein the alkyl groups have 1–3 carbon atoms and the substituent(s) is halo, dihalo, amino, aminoalkyl, hydroxy, lower alkoxy or lower alkyl;

$R^2$ and $R^7$ are hydrogen;

$R^3$ is lower alkyl or amino lower alkyl;

$R^4$ and $R^5$ can be joined together through the carbon and nitrogen atoms to which they are attached to form a ring of the formula:

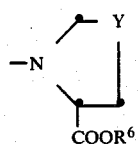

wherein Y is $CH_2$, S, or $CH-OCH_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Still more preferred antihypertensive compounds of Formula VI are those wherein:

R and $R^6$ can each independently be hydroxy, lower alkoxy, aralkyloxy;

$R^2$ and $R^7$ are hydrogen;

$R^3$ is methyl, aminoloweralkyl;

$R^4$ and $R^5$ are joined through the carbon and nitrogen atoms to form proline, 4-thiaproline or 4-methoxyproline and;

$R^1$ is alkyl having from 1–8 carbon atoms, substituted lower alkyl wherein the alkyl group has 1–5 carbon atoms and the substituent is amino, arylthio or aryloxy, aralkyl or heteroaralkyl wherein the alkyl portion has 1–3 carbon atoms, substituted aralkyl or heteroaralkyl wherein the alkyl groups have 1–3 carbon atoms and the substituent(s) is halo, dihalo, amino, aminoalkyl, hydroxy, lower alkoxy or lower alkyl; and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Examples of Formula VI compounds are:

(i) N-(1-carboxy-3-phenylpropyl)-L-alanyl-L-proline;

(ii) N-(1-ethoxycarbonyl-3-phenylpropyl)-L-alanyl-L-proline;

(iii) N-(1-ethoxycarbonyl-4-methylpentyl)-L-alanyl-L-proline;

(iv) N-(1-carboxy-5-aminopentyl)-L-alanyl-L-proline;

(v) N-α-(1-carboxy-3-phenylpropyl)-L-lysyl-L-proline;

(vi) N-α-(1-ethoxycarbonyl-3-phenylpropyl)-L-lysyl-L-proline;

(vii) N-α-[1-carboxy-3-(3-indolyl)-propyl]-L-lysyl-L-proline;

(viii) N-α-[1-carboxy-3-(4-chlorophenyl)-propyl]-L-lysyl-L-proline;

(ix) N-α-[1-carboxy-2-phenylthioethyl]-L-lysyl-L-proline;

(x) N-α-[1-carboxy-3-(4-chlorophenyl)-propyl]-L-lysyl-trans-4-methoxy-L-proline;

(xi) N-α-[1-carboxy-5-aminopentyl]-L-lysyl-L-proline;

(xii) N-α-(1-carboxy-3-phenylpropyl)-L-ornithyl-L-proline;

(xiii) ethyl N-(1-ethoxycarbonyl-3-phenylpropyl)-L-alanyl-L-prolinate hydrochloride;

(xiv) N-[1-(ethoxycarbonyl)-3-(4-imidazolyl)propyl]-L-alanyl-L-proline.

(xv) N-[1-carboxy-3-(4-imidazolyl)propyl]-L-lysyl-L-proline;

(xvi) N-(1(S)-carboxy-3-phenylpropyl)-L-alanyl-L-proline;

(xvii) N-(1(S)-ethoxycarbonyl-3-phenylpropyl)-L-alanyl-L-proline maleate salt;

(xviii) N-α-(1(S)-carboxy-3-phenylpropyl)-L-lysyl-L-proline;

(xix) ethyl N-(1(S)-ethoxycarbonyl-3-phenylpropyl)-L-alanyl-L-prolinate hydrochloride;

(xx) N-α-(1(S)-ethoxycarbonyl-3-phenylpropyl)-L-lysyl-L-proline.

The above-described Formula VI compounds, their use and the method of preparation thereof are disclosed in U.S. Pat. No. 4,374,829 the disclosure of which is hereby incorporated herein by reference.

The combination composition of the invention can contain varying amounts of the Formula I or IA (i) antithrombotic compound and Formula VI (ii) antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Treatment dosage for human beings for cardiovascular use can be varied as necessary. Generally, daily dosages of the composition of the invention can range from about 6000 to about 10 mg; preferably, from about 3000 to about 20 mg.

The amount of active ingredient that may be combined with the carrier materials to produce a single dosage form for cardiovascular use will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 20 mg to about 500 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The composition of this invention inhibits platelet accumulation at the damaged endothelial surface via the Formula I or IA compound. This inhibitory effect is potentiated by the presence of the antihypertensive compound.

Thus, the compositions of the invention are useful in treating thrombosis and are also of value in the management of acute and chronic congestive heart failure.

In vivo testing of the composition of this invention in test animals (rabbits) may be used to demonstrate that this composition is pharmaceutically effective in decreasing platelet-related arterial thrombic formation.

To demonstrate the potentiation of the antihypertensive compound on the anti-thrombotic Formula I or IA compound comprising the combination composition of the invention, the effect of these compounds on test animals (rabbits) may be determined separately and then in combination. The effect of a different class of antihypertensive agents singly and in combination with the Formula I or IA compound of the invention may also be determined for comparative purposes. The methods employed are described in a copending application, attorney docket number 17062, U.S. Ser. No. 617,293, filed June 4, 1984, which is hereby incorporated herein by reference.

For use where a composition for intravenous administration is employed, a suitable dosage range is from 0.2 to 10 mg (preferably 1 to 8 mg) of a compound of Formulae I and/or IA per kg of body weight per day and in the case where an oral composition is employed a suitable dosage range is about 1 to 50 mg of a compound of Formulae I and/or IA per kg of body weight per day, preferably from 10 to 40 mg/kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg to 500 mg of the active ingredient and each cachet or capsule contains from 50 mg to 500 mg of the active ingredient.

The best mode contemplated by applicants for carrying out their invention is illustrated in the following working examples. No limitation, however, is intended except as set forth in the appended claims.

EXAMPLE 1

2-Cyano-6H-dibenz[b,e][1,4]oxathiepin

Step A: 2-(o-Methoxyphenylthio)benzoic acid

Stir under reflux for 3 hours a mixture of 70 gm (0.5 mole) of o-methoxythiophenol, 120.5 gm (0.486 mole) of o-iodobenzoic acid, 81.7 gm (1.46 mole) of potassium hydroxide, 85 gm (1.34 mole) of copper powder and 800 cc of water. Filter the reaction mixture hot and again filter the filtrate through celite. Acidify the filtrate with concentrated hydrochloric acid. Separate the precipitate, wash well with water and dry in vacuo at 70° C. to obtain the title product. (m.p. 198°-200° C.).

Step B: Methyl 2-(o-methoxyphenylthio)benzoate

Dissolve 115 gm of the acid of Step A in 3.5 l. of methanol and add slowly 25 cc of sulfuric acid. Stir under reflux for 72 hours. Cool the reaction mixture to room temperature and add 100 gm of sodium bicarbonate in portions. Stir for an additional hour, filter and strip the filtrate to dryness. Dissolve the residue in methylene chloride and wash the solution three times with water. Dry the solution and strip to an oil which solidifies. (m.p. 82°-84° C.).

Step C: 3-(o-Carbomethoxyphenylthio)-4-methoxybenzaldehyde

Dissolve 117 gm (0.427 mole) of the ester of Step B in 1500 cc of 1,2-dichloroethane and cool with stirring in an ice-bath. Add 200 cc (345 gm, 1.82 mole) of titanium tetrachloride at a rapid dropwise rate. Add also fairly rapidly 154 gm (1.34 mole) of dichloromethyl methyl ether. Stir the mixture under a nitrogen atmosphere overnight then pour into ice. After shaking, separate the organic phase and extract the aqueous phase twice with methylene chloride. Wash the combined organic phases twice with water, dry and strip to an oil which crystallizes. (m.p. 99°-104° C.).

Step D: 3-(o-Carboxyphenylthio)-4-hydroxybenzaldehyde

Heat 126 gm of the aldehyde of Step C in a mixture of 1500 cc of glacial acetic acid and 1500 cc of 48% hydrogen bromide in an oil bath at 150° C. with mechanical stirring until no trace of non-demethylated product remains (4-5 days). Cool the reaction mixture and pour into 7 l. of water. Separate the precipitate, wash well with water and dry in vacuo at 70° C. to constant weight. The material is used in the following step without further purification.

Step E: 3-(o-Carboxyphenylthio)-4-hydroxybenzonitrile

Reflux 91.3 gm of the aldehyde of Step D, 27.4 gm of hydroxylamine hydrochloride and 41.9 gm of sodium formate in 900 cc of formic acid (98-100%) for 1¼ hours. Cool the mixture and pour into 2½ l. of cold water. Separate the precipitate, wash with water and dry in vacuo at 75° C. The material is sufficiently pure for utilization in the subsequent step.

Step F: 2-Cyano-6H-6-oxo-dibenz[b,e][1,4]oxathiepin

Stir together at room temperature overnight 8.4 gm of the nitrile of Step E and 19.16 gm (3 molar equivalents) of dicyclohexylcarbodiimide in 400 cc of ethyl acetate. Filter the reaction mixture to remove dicyclohexyl urea. Strip the filtrate to dryness. Triturate the residue in a small volume of ethyl acetate and filter to obtain the product which is used directly in the next step.

Step G: 3-(o-Hydroxymethylphenylthio)-4-hydroxybenzonitrile

Dissolve 31.24 gm (0.123 mole) of the nitrile of Step F in 750 cc of tetrahydrofuran and add 10.4 gm (0.274 moles) of sodium borohydride. Stir the solution at room temperature for 1½ hours. Add water in small portions until foaming ceases. Remove the tetrahydrofuran by evaporation. Shake the residue with ethyl acetate, water and dilute hydrochloric acid. Separate the organic phase and extract the aqueous phase three times with ethyl acetate. Wash the combined organic phases with two small volumes of water, dry and strip to a thick oil which is used as such for the following step.

Step H: 2-Cyano-6H-dibenz[b,e][1,4]oxathiepin

Stir the crude nitrile of Step F(assumed 100% yield, 0.123 mole) and 38 gm (50% excess) of dicyclohexylcarbodiimide at 105°–110° C. for 1½ hours. Cool the reaction mixture and extract with methylene chloride. Filter to remove the dicyclohexyl urea and strip the filtrate to dryness. Triturate in a small volume of ethyl acetate, filter and strip to dryness. Extract four times with hot benzene and strip the combined extracts to dryness. Chromatograph on a silica gel column, eluting with benzene to obtain the title product. (m.p. 145°–147° C.).

EXAMPLE 2

6H-Dibenz[b,e][1,4]oxathiepin-2-carboxylic acid

Reflux 3.2 gm of the nitrile of Example 1 for 5 hours in a mixture of 50 cc of 20% sodium hydroxide and 50 cc of ethanol. Allow the resulting clear solution to stand at room temperature overnight. Evaporate the ethanol. Dilute the residue with 200 cc of water and heat on a steam bath to dissolve. Filter and acidify the filtrate. Separate the precipitate, wash and dry in vacuo at 75° C. to obtain the title product. (m.p. 225°–227° C.).

EXAMPLE 3

6H-Dibenz[b,e][1,4]oxathiepin-2-carboxylic acid-11,11-dioxide

Suspend 1.3 gm of the acid of Example 2 in 50 cc of glacial acetic acid and add 7 cc of 30% hydrogen peroxide. Heat slowly to 75° C. and stir for 5 hours. Allow the reaction mixture to stand at room temperature overnight. Separate the precipitate, wash with acetic acid and dry to obtain the title product. (m.p. 279°–282° C.).

EXAMPLE 4

2-Hydroxymethyl-6H-dibenz[b,e][1,4]oxathiepin

Dissolve 10 mmoles of 6H-dibenz[b,e][1,4]oxathiepin-2-carboxylic acid in 75 cc tetrahydrofuran, add slowly at ambient temperature 12 cc of a 1 molar solution of borane in tetrahydrofuran, stir for 3 hours, add 20 cc water, evaporate the tetrahydrofuran, dilute the residue with water and filter. Crystallize the crude product from ethanol.

EXAMPLE 5

2-Hydroxymethyl-6H-dibenz[b,e][1,4]oxathiepin-11,11-dioxide 725 mg (2.5 mmoles) of the acid prepared in Example 3, above were dissolved, in 25 cc THF, and there was added 303 mg triethylamine (3 mmoles). The resulting solution was cooled in an ice and water bath, then 298 mg ethyl chloroformate (2.75 mmoles) was added slowly; there was precipitation of Et$_3$N.HCl. The suspension was stirred in the cold for 5 minutes, then there was added 95 mg NaBH$_4$ (2.5 mmoles) and, slowly, 1 cc water; the mixture frothed gently. After stirring for 1 hour in the cold, the cooling bath was removed and the mixture allowed to warm to room temperature and diluted with 5 cc water. The THF was evaporated away and the residual aqueous residue extracted with EtOAc. Extracts were washed with water three times, dried and stripped to a colorless oil containing solids. Thin layer chromatography shows 4–5 spots at this stage. A sample was taken, dissolved in THF and treated with addition of NaBH$_4$/H$_2$O and these several spots changed into two; the bulk of the product was given the same treatment after the same workup as before, the crude mixture of two products was chromatographed on silica gel, and a white solid was obtained (most polar compound), triturated in hexane and filtered, to yield the title compound, 305 mg, m.p. 148–150, Calc'd: C: 60.85, H: 4.38, S: 11.60; Found: 60.91, 4.45, 11.47.

EXAMPLE 6

6H-Dibenz[b,e][1,4]oxathiepin-2-carboxaldehyde-11,11-dioxide

To a solution of 552 mg (2 mmoles) of 2-hydroxymethyl-6H-dibenz[b,e][1,4]oxathiepin-11,11-dioxide (from Example 5) in 40 cc methylene chloride there was added 650 mg (3 mmoles) of pyridinium chlorochromate. After three hours of stirring at room temperature, the reaction mixture was filtered through a bed of celite. The residue obtained an evaporation of the filtrate to dryness was chromatographed on a column of silica gel, using as eluent a 1:4 mixture of ethyl acetate and toluene, to afford 530 mg of the adldehyde as a white solid, m.p. 190–192. Calcd.: C, 61.30; H, 3.67; S, 11.69. Found: C, 61.41; H, 3.57; S, 12.03.

EXAMPLE 7

6H-Dibenz[b,e][1,4]oxathiepin-2-carboxylic acid

Step A: 3-(o-(Hydroxymethyl)phenylthio)-4-hydroxybenzoic acid

A mixture of 25 gm o-mercaptobenzyl alcohol (0.18 mole), 39.6 gm 3-iodo-4-hydroxy benzoic acid (0.15 mole), 11.43 g copper powder (0.18 mole), 70 cc 40% aqueous potassium hydroxide solution (0.5 mole) and 300 cc water was placed under nitrogen atmosphere and stirred under reflux for 18 hours. After cooling the mixture was diluted with 400 cc of water and extracted twice with 100 cc of ethyl acetate to remove neutral products. The aqueous fraction was filtered and the filtrate acidified with conc. HCl to afford the title compound as an oil which solidified and was filtered. There was obtained 32.8 g of solid product.

Step B: Methyl 3-(o-(hydroxymethyl)phenylthio)-4-hydroxy-benzoate 32.5 gm of the acid prepared in Step A was refluxed in 1000 cc methanol containing 1 cc sulfuric acid for 2 days; the methanol was evaporated away and the residue dissolved in 1 liter of ethyl acetate and the solution washed with water, 10% aqueous sodium bicarbonate solution and water again, dried over sodium sulfate and evaporated to an oil which crystallized on standing, 34 g.

Step C: Methyl 6H-dibenz[b,e][1,4]oxathiepin-2-carboxylate

The 34 g ester from Step B (0.111 mole) was dissolved in 650 cc tetrahydrofuran, and there was added 23.4 g diethylazo dicarboxylate (0.134 mole); the resulting solution was cooled to 0° C., and a solution of 32.3 g triphenylphosphine (0.123 mole) in 250 cc tetrahydrofuran was added dropwise. The resulting solution was stirred in the cold for an additional 30 minutes. The solvent was evaporated away and to the residue was added 700 cc carbon tetrachloride. The mixture was stirred at room temperature for 30 minutes then the insolubles were filtered and the filtrate evaporated down to an oil which was crude title product and which was hydrolyzed as such without further purification.

Step D: 6H-Dibenz[b,e][1,4]oxathiepin-2-carboxylic acid

The crude ester from Step C was refluxed gently in a mixture of 500 cc 20% aqueous sodium hydroxide solution and 500 cc tetrahydrofuran for 16 hours. After cooling, the layers were separated; the organic layer was evaporated down, and the residue diluted with 1 liter of water. Insolubles were filtered, and the filtrate was extracted twice with ethyl acetate, then it was acidified with concentrated HCl, affording on filtration 23 grams of the crude title compound. This was heated on a steam bath with 280 cc glacial acetic acid, and the mixture filtered while hot. The filtrate was concentrated to a volume of 100 cc, the resulting suspension heated again for 15 minutes then allowed to cool and stand at room temperature overnight. Filtration afforded 15.9 grams of purified product, m.p.: 225°–227°.

EXAMPLE 8

6H-Dibenz[b,e][1,4]oxathiepin-2-carboxylic acid-11-oxide

Dissolve with warming 380 mg of the carboxylic acid of Example 7 in 38 cc of glacial acetic acid. Place the reaction mixture in an oil bath at 40° C. and, after equilibration, add 1.5 cc of 30% hydrogen peroxide. Stir the mixture at 40° C. for 3½ hours until solution clears. Dilute with 300 cc of water and separate the precipitate by filtration to obtain the title product. (m.p. 284°–286° dec.).

EXAMPLE 9

2-Hydroxymethyl-6H-dibenz[b,e][1,4]oxathiepin-11-oxide

Dissolve 10 mmoles of 6H-dibenz[b,e][1,4]oxathiepin-2-carboxylic acid-11-oxide in 75 cc tetrahydrofuran, add slowly at ambient temperature 12 cc of a 1 molar solution of borane in tetrahydrofuran, stir for 3 hours, add 20 cc water, evaporate the tetrahydrofuran, dilute the residue with water and filter. Crystallize the crude product from ethanol.

EXAMPLE 10

6H-Dibenz[b,e][1,4]oxathiepin-2-carboxaldehyde-11-oxide

The procedure described in Example 6 is applied, substituting 2-hydroxymethyl-6H-dibenz[b,e][1,4]oxathiepin-11-oxide from Example 9 for the corresponding 11,11-dioxide, to obtain the title compound.

EXAMPLE 11

8-Fluoro-6H-dibenz[b,e][1,4]oxathiepin-2-carboxaldehyde-11-oxide

To a solution of 8-fluoro-2-hydroxymethyl-6H-dibenz[b,e][1,4]oxathiepin (85 mg, 0.324 mmole) in CH$_2$Cl$_2$ (10 ml) add m-chloroperbenzoic acid (68 mg, 0.33 mole) and stir the mixture at room temperature for 16 hours. Add Ca(OH)$_2$ (0.5 g) and stir for 20 minutes, then filter through a bed of Celite (diatomaceous earth). Evaporate the filtrate and slurry the solid residue with hexane (20 ml) and filter the insoluble material to obtain 8-fluoro-2-hydroxymethyl-6H-dibenz[b,e][1,4]oxathiepin-11-oxide.

Apply the procedure described in Example 6, substituting 8-fluoro-2-hydroxymethyl-6H-dibenz[b,e][1,4]oxathiepin-11-oxide for 2-hydroxymethyl-6H-dibenz[b,e][1,4]oxathiepin-11,11-dioxide, to afford the title compound.

EXAMPLE 12

8-Fluoro-6H-dibenz[b,e][1,4]oxathiepin-2-carboxaldehyde-11,11-dioxide

The procedure described in Example 6 is applied, substituting 8-fluoro-2-hydroxymethyl-6H-dibenz[b,e][1,4]oxathiepin-11,11-dioxide for 2-hydroxymethyl-6H-dibenz[b,e][1,4]oxathiepin 11,11-dioxide to afford the title compound.

EXAMPLE 13

9-Fluoro-6H-dibenz[b,e][1,4]oxathiepin-2-carboxaldehyde-11-oxide

To a solution of 9-fluoro-2-hydroxymethyl-6H-dibenz[b,e][1,4]oxathiepin (170 mg, 0.65 mmole) in CH$_2$Cl$_2$ (25 ml) add m-chloroperbenzoic acid (136 mg, 0.66 mmole) and stir at room temperature for 18 hours. Add Ca(OH)$_2$ (0.5 g) and stir for 25 minutes, then filter through a bed of Celite. Evaporate the filtrate and slurry the residue with hexane (50 ml) and filter the insoluble material to obtain 9-fluoro-2-hydroxymethyl-6H-dibenz[b,e][1,4]oxathiepin-11-oxide.

Apply the procedure described in Example 6, substituting 9-fluoro-2-hydroxymethyl-6H-dibenz[b,e][1,4]oxathiepin-11-oxide for 2-hydroxymethyl-6H-dibenz[b,e][1,4]oxathiepin-11,11-dioxide, to afford the title compound.

EXAMPLE 14

9-Fluoro-6H-dibenz[b,e][1,4]oxathiepin-2-carboxaldehyde-11,11-dioxide

The procedure described in Example 6 is applied, substituting 9-fluoro-2-hydroxymethyl-6H-dibenz[b,e][1,4]oxathiepin-11,11-dioxide for 2-hydroxymethyl-6H-dibenz[b,e][1,4]oxathiepin-11,11-dioxide to afford the title compound.

EXAMPLE 15

6H-Dibenz[b,e][1,4]oxathiepin-9-carboxaldehyde-11,11-dioxide

The procedure described in Example 6 is applied, substituting 9-hydroxymethyl-6H-dibenz [b,e][1,4]oxathiepin-11,11-dioxide for the 2-hydroxymethyl analog, to afford the title compound.

EXAMPLE 16

2-(N-phenyliminomethyl)-6H-dibenz[b,e][1,4]oxathiepin-11,11-dioxide

A mixture of 0.01 mole of 6H-dibenz [b,e][1,4]oxathiepin-2-carboxaldehyde-11,11dioxide (from Example 6) and 0.01 mole of aniline in 150 ml benzene is heated at reflux, with azeotropic removal of water, to afford the title compound.

EXAMPLE 17

9-Cyano-6H-dibenz[b,e][1,4]oxathiepin

Step A: 2-(o-Aminophenylthio)-4-nitrobenzoic acid

Heat a mixture of 466 g (3.72 moles) of 2-aminothiophenol, 250 g (1.24 moles) of 2-chloro-4-nitrobenzoic acid, 1.25 l of quinoline, 192 g (1.34 moles) of cuprous oxide and 125 ml of pyridine in an oil bath at 160°–170° C. with mechanical stirring for 90 minutes. Cool the mixture to room temperature and add 1.87 l of concentrated hydrochloric acid followed by 625 ml of water. Separate the precipitate and wash well with water. Extract the washed precipitate into boiling methanol and filter. Treat the hot filtrate with charcoal, filter and strip to dryness. Dissolve the residue in aqueous sodium hydroxide, filter and treat with charcoal. Acidify the filtrate and separate the precipitate. (Yield: 38 g).

Additional Crop

Take up the insoluble residue from the basic extraction into water, filter through celite and acidify. Separate the precipitate and dissolve in ethyl acetate. Treat with charcoal, filter and strip to dryness. (Yield: 23 g).

Step B: 2-(o-Hydroxyphenylthio)-4-nitrobenzoic acid

Suspend 10.15 g (35 mmoles) of the amino acid of Step A in 75 ml of water and add 4 ml concentrated sulfuric acid (7.36 g, 75 mmoles, 150 meq). Cool the mixture in an ice-bath and add 3.657 g (53 mmoles) of sodium nitrite in portions at 0°–5° C. Stir the suspension in the cold for 20 minutes. Add 10 g (91 mmoles) of sodium fluoroborate and stir for an additional 20 minutes. Separate the precipitated crude diazonium fluoroborate, suspend the precipitate in 250 ml of 50% sulfuric acid and heat in an oil bath at 90°–100° C. for 45 minutes. Cool the mixture and separate the precipitate. (Yield: 7.76 g).

Step C: 2-(o-Hydroxyphenylthio)-4-nitrobenzyl alcohol

Dissolve 42 g (0.144 mole) of the acid of Step B in 575 ml of tetrahydrofuran and add dropwise 275 ml of borane (0.275 mole BH$_3$) in tetrahydrofuran (as a 1 molar solution) under a nitrogen atmosphere at room temperature. Stir at room temperature overnight. Slowly add excess water and concentrate to remove the tetrahydrofuran. Extract into ethyl acetate and add 120 g of silica gel to the ethyl acetate solution. Place the mixture atop a column of 1500 g of silica gel and elute with 20% ethyl acetate/benzene to obtain the pure diol. (m.p. 131°–133° C.).

Step D: 9-Nitro-6H-dibenz[b,e][1,4]oxathiepin

Stir 4.6 g of the diol of Step C and 17.1 g (5 molar equivalents) of dicyclohexylcarbodiimide together at 110°–115° C. for 4–5 hours. Cool the mixture, dissolve in 250 ml of tetrahydrofuran and filter. Add silica gel to the filtrate and strip to dryness. Place the residue atop a column of 310 g of silica gel and elute with 50:50 benzene/hexane. Strip to dryness to obtain the title product (m.p. 112°–113° C.).

Step E: 9-Amino-6H-dibenz[b,e][1-4]oxathiepin

Dissolve 7.92 g of the nitro compound of Step D in 150 ml of tetrahydrofuran and add 50 ml of concentrated hydrochloric acid. Place the mixture in a cold water bath and add 22.7 g (3 molar equivalents 10%) of stannous chloride dihydrate in portions. Stir at room temperature for 5½ hours. Dilute the reaction mixture with water, basify with 40% aqueous sodium hydroxide and extract with ethyl acetate. Wash the organics with water, dry and strip to dryness. (Yield: 7.22 g crude amine).

Step F: 9-Cyano-6H-dibenz[b,e][1,4]oxathiepin

Suspend 1.55 g (6.77 mmoles) of the amine of Step E in 36 ml of 1N hydrochloric acid and cool the mixture in an ice bath. Add slowly a solution of 502 mg (7.28 mmoles) of sodium nitrite in 10 ml of water, keeping the temperature at 0°–5° C. Stir the mixture in the cold for 15 minutes. Neutralize to pH 7 with aqueous sodium carbonate solution. Add the mixture slowly to a cooled mixture of 1.37 g (15.3 mmoles) of cuprous cyanide and 2.0 g (30.8 mmoles) of potassium cyanide in 50 ml of water at 0°–5° C. Recover the precipitate by filtration and wash well with water. Dissolve the precipitate in tetrahydrofuran, add silica gel and evaporate the tetrahydrofuran. Place the residue atop a silica gel column and elute with 50:50 benzene/hexane. Remove the solvent to obtain the title product. (m.p. 136°–137° C.).

EXAMPLE 18

9-Cyano-6H-dibenz[b,e][1,4]oxathiepin-11,11-dioxide

Dissolve 850 mg (3.56 mmole) of the 9-cyano-6H-dibenz[b,e][1,4]oxathiepin of Example 17 in 50 ml of methylene chloride. Add 2.3 g (11.3 mmole) of 85% m-chloroperbenzoic acid and stir at room temperature for 2 hours. Add excess calcium hydroxide and continue stirring for a few minutes. Filter the reaction mixture through celite and strip the filtrate to dryness. Chromatograph the residue on silica gel eluting with 25% ethyl acetate in benzene to obtain the title product. (m.p. 177°–179° C.).

EXAMPLE 19

6H-Dibenz[b,e][1,4]oxathiepin-9-carboxaldehyde

To a stirred solution of 850 mg (3.56 mmole) of the 9-cyano-6H-dibenz[b,e][1,4]oxathiepin of Example 17 in 25 ml formic acid is added a 1:1 alloy of nickel and aluminum (50 mg). The mixture is heated at reflux for 16 hours. The solvent is removed in vacuo and the residue purified by chromatography on silica gel to afford the title compound.

EXAMPLE 20

6H-Dibenz[b,e][1,4]oxathiepin-2-carboxaldehyde

Follow the procedure of Example 19, but substitute the 2-cyano-6H-dibenz[b,e][1,4]oxathiepin of Example 1, for the 9-cyano-6H-dibenz[b,e][1,4]oxathiepin of Example 17, to obtain the title compound.

EXAMPLE 21

6H-Dibenz[b,e][1,4]oxathiepin-9-carboxaldehyde-11-oxide

Apply the procedure described in Example 6, substituting 9-hydroxymethyl-6H-dibenz[b,e][1,4]oxathiepin-11-oxide for 2-hydroxymethyl-6H-dibenz[b,e][1,4]oxathiepin 11,11-dioxide to afford the title compound.

EXAMPLE 22

2-Fluoro-6H-dibenz[b,e][1,4]oxathiepin-9-carboxaldehyde-11-oxide

Apply the procedure described in Example 6, substituting 2-fluoro-9-hydroxymethyl-6H-dibenz[b,e][1,4]oxathiepin-11-oxide for 2-hydroxymethyl-6H-dibenz[b,e][1,4]oxathiepin 11,11-dioxide to afford the title compound.

EXAMPLE 23

3-Fluoro-6H-dibenz[b,e][1,4]oxathiepin-9-carboxaldehyde-11-oxide

Apply the procedure described in Example 6, substituting 3-fluoro-9-hydroxymethyl-6H-dibenz[b,e][1,4]oxathiepin-11-oxide for 2-hydroxymethyl-6H-dibenz[b,e][1,4]oxathiepin 11,11-dioxide to afford the title compound.

EXAMPLE 24

2-Fluoro-6H-dibenz[b,e][1,4]oxathiepin-9-carboxaldahyde-11,11-dioxide

Apply the procedure described in Example 6, substituting 2-fluoro-9-hydroxymethyl-6H-dibenz[b,e][1,-4]oxathiepin-11,11-dioxide for 2-hydroxymethyl-6H-dibenz[b,e][1,4]oxathiepin 11,11-dioxide to afford the title compound.

EXAMPLE 25

3-Fluoro-6H-dibenz[b,e][1,4]oxathiepin-9-carboxaldehyde-11,11-dioxide

Apply the procedure described in Example 6, substituting 3-fluoro-9-hydroxymethyl-6H-dibenz[b,e][1,-4]oxathiepin-11,11-dioxide for 2-hydroxymethyl-6H-dibenz[b,e][1,4]oxathiepin 11,11-dioxide to afford the title compound.

What is claimed is:
1. Compounds of the formulae:

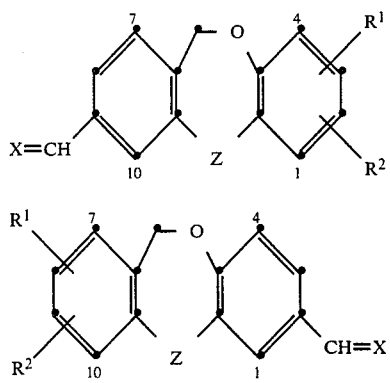

wherein

Z is thio, sulfinyl, or sulfonyl;

$R^1$ and $R^2$ are independently hydrogen, halogen, amino, $C_1$ to $C_4$ alkyl, $C_1$ to $C_4$ alkylthio, $C_1$ to $C_4$ alkoxy, thiol, $C_1$ to $C_4$ alkylsulfinyl, $C_1$ to $C_4$ alkylsulfonyl, trifluoromethyl, trifluoromethylthio, cyano, nitro, $C_1$ to $C_5$ alkyl having one of the hydrogens replaced by phenyl, halophenyl, nitrophenyl, aminophenyl or loweralkylphenyl, hydroxyloweralkyl, $C_1$ to $C_4$ alkylamino, dialkylamino wherein each alkyl group has 1 to 4 carbons;

X is O, N—$R^3$, wherein $R^3$ is hydrogen, $C_1$ to $C_4$ alkyl, phenyl, halophenyl, nitrophenyl, aminophenyl, hydroxyphenyl, loweralkylphenyl, hydroxy, $C_1$ to $C_4$ alkoxy, $C_1$ to $C_5$ alkanoyloxy, amino, $C_1$ to $C_4$ alkylamino or dialkylamino wherein each alkyl group has 1 to 4 carbons; and the pharmaceutically acceptable salts thereof.

2. A compound according to claim 1, said compound having the Formula IA wherein Z is sulfinyl or sulfonyl, $R^2$ is hydrogen and $R^1$ is at position 8 or 9 and is fluoro, chloro, bromo, amino or hydrogen, or said compound having the Formula I wherein Z is sulfinyl or sulfonyl, $R^2$ is hydrogen and $R^1$ is at position 2 or 3 and is fluoro, chloro, bromo, amino or hydrogen.

3. A compound according to claim 1, said compound having the Formula IA wherein Z is sulfinyl or sulfonyl, $R^2$ is hydrogen, $R^1$ is at position 8 or 9 and is fluoro, chloro, bromo, amino, or hydrogen, and X is oxo, or said compound having the Formula I wherein Z is sulfinyl or sulfonyl, $R^2$ is hydrogen, $R^1$ is at position 2 or 3 and is fluoro, chloro, bromo, amino or hydrogen, and X is oxo.

4. A compound according to claim 1, said compound having the Formula IA wherein Z is sulfonyl, $R^2$ is hydrogen and $R^1$ is at position 8 or 9 and is fluoro, chloro, bromo, amino, or hydrogen, and X is oxo, or said compound having the Formula I wherein Z is sulfonyl, $R^2$ is hydrogen, $R^1$ is at position 2 or 3 and is fluoro, chloro, bromo, amino or hydrogen, and X is oxo.

5. The compound of claim 1 which is: 6H-dibenz[b,e][1,4]oxathiepin-2-carboxaldehyde-11,11-dioxide.

6. The compound of claim 1 which is: 8-fluoro-6H-dibenz[b,e][1,4]oxathiepin-2-carboxaldehyde-11,11-dioxide.

7. The compound of claim 1 which is: 9-fluoro-6H-dibenz[b,e][1,4]oxathiepin-2-carboxaldehyde-11,11-dioxide.

8. The compound of claim 1 which is: 6H-dibenz[b,e][1,4]oxathiepin-9-carboxaldehyde-11,11-dioxide.

9. The compound of claim 1 which is: 2-fluoro-6H-dibenz[b,e][1,4]oxathiepin-9-carboxaldehyde-11,11-dioxide.

10. The compound of claim 1 which is: 3-fluoro-6H-dibenz[b,e][1,4]oxathiepin-9-carboxaldehyde-11,11-dioxide.

11. The compound of claim 1 which is: 6H-dibenz[b,e][1,4]oxathiepin-2-carboxaldehyde-11-oxide.

12. The compound of claim 1 which is: 8-Fluro-6H-dibenz[b,e][1,4]oxathiepin-2-carboxaldehyde-11-oxide.

13. The compound of claim 1 which is: 9-Fluoro-6H-dibenz[b,e][1,4]oxathiepin-2-carboxaldehyde-11-oxide.

14. The compound of claim 1 which is: 3-Fluoro-6H-dibenz[b,e][1,4]oxathiepin-9-carboxaldehyde-11-oxide.

15. The compound of claim 1 which is: 2-(N-phenyliminomethyl)-6H-dibenz[b,e][1,4]oxathiepin-10,11-dioxide.

16. The compound of claim 1 which is: 6H-dibenz[b,e][1,4]oxathiepin-9-carboxaldehyde.

17. The compound of claim 1 which is: 6H-dibenz[b,e][1,4]oxathiepin-2-carboxaldehyde.

18. The compound of claim 1 which is: 6H-dibenz[b,e][1,4]oxathiepin-9-carboxaldehyde-11-oxide.

19. The compound of claim 1 which is: 2-fluoro-6H-dibenz[b,e][1,4]oxathiepin-9-carboxaldehyde-11-oxide.

20. A pharmaceutical composition for treating or controlling allergic conditions or thromboembolic diseases in a mammal comprising a pharmaceutically-effective amount of a compound of claim 1.

21. A pharmaceutical composition according to claim 20 additionally comprising an effective amount of a second active ingredient selected from the group consisting of indomethacin, ibuprofen, sulindac, fenbufen, zomepirac, diflunisal, benadryl, dramamine, histadyl, phenergan, captopril, N-(1-ethoxycarbonyl-3-phenylpropyl)-L-alanyl-L-proline, N-(1(S)-carboxy-3-phenylpropyl)-L-alanyl-L-proline and N-α-(1-carboxy-3-phenylpropyl)-L-lysyl-L-proline.

22. A method of treating or controlling allergic conditions in a mammal comprising administering to a mammal in need of such treatment a pharmaceutically-effective amount of a compound of claim 1.

23. A method of treating or preventing thromboembolic diseases in a mammal comprising administering to a mammal in need of such treatment a pharmaceutically-effective amount of a compound according to claim 1 and a pharmaceutically-acceptable carrier.

* * * * *